(12) United States Patent
Naddaka et al.

(10) Patent No.: US 7,943,771 B2
(45) Date of Patent: May 17, 2011

(54) IMIQUIMOD PRODUCTION PROCESS

(75) Inventors: Vladimir Naddaka, Petch-Tikva (IL); Eyal Klopfer, Tel Aviv (IL); Shady Saeed, Haifa (IL); Stephen Cherkez, Caesarea (IL); Oded Arad, Rehovot (IL)

(73) Assignee: Chemagis Ltd., Bnei Brak (IL)

( * ) Notice: Subject to any disclaimer, the term of this patent is extended or adjusted under 35 U.S.C. 154(b) by 1059 days.

(21) Appl. No.: 11/626,764

(22) Filed: Jan. 24, 2007

(65) Prior Publication Data
US 2008/0177074 A1    Jul. 24, 2008

(51) Int. Cl.
C07D 487/04    (2006.01)
(52) U.S. Cl. ........................................... 546/82
(58) Field of Classification Search ............. 546/82
See application file for complete search history.

(56) References Cited

U.S. PATENT DOCUMENTS

| | | | |
|---|---|---|---|
| 4,689,338 | A | 8/1987 | Gerster |
| 4,929,624 | A | 5/1990 | Gerster et al. |
| 4,988,815 | A | 1/1991 | André et al. |
| 5,175,296 | A | 12/1992 | Gerster |
| 5,367,076 | A | 11/1994 | Gerster |
| 5,633,406 | A * | 5/1997 | Mitchell et al. .............. 564/395 |
| 7,323,568 | B2 | 1/2008 | Naddaka et al. |
| 2005/0085500 | A1 | 4/2005 | Gutman et al. |
| 2006/0004202 | A1 | 1/2006 | Razzetti et al. |
| 2007/0010675 | A1 | 1/2007 | Allegrini et al. |
| 2007/0135640 | A1 | 6/2007 | Naddaka et al. |
| 2008/0194822 | A1 | 8/2008 | Naddaka et al. |

FOREIGN PATENT DOCUMENTS

| | | |
|---|---|---|
| EP | 1609792 A1 | 12/2005 |
| WO | WO 2005/033049 A2 | 4/2005 |
| WO | WO 2005/033049 A3 | 4/2005 |
| WO | WO 2006/070379 A1 | 7/2006 |
| WO | WO 2006/100226 A1 | 9/2006 |
| WO | WO 2008/090550 A2 | 7/2008 |
| WO | WO 2008/090550 A3 | 7/2008 |
| WO | WO 2008/099377 A2 | 8/2008 |
| WO | WO 2008/099377 A3 | 8/2008 |

OTHER PUBLICATIONS

Sarges et al., "4-Amino[1,2,4]triazolo[4,3-a]quinoxalines. A novel class of potent adenosine receptor antagonists and potential rapid-onset antidepressants", J. Med Chem, vol. 33, No. 8, pp. 2240-2254 (Aug. 1990).

Bredereck et al., "Umsetzungen von Halogenverbindungen mit Formamid (Formamid-Reaktionen, III. Mitteilung. II. Mitteil.: G. Theilig, Chem. Ber. 86, 96 [1953])," Chemische Berichte, 87(4), 537-546 (1954).

P. Jacobson, "Ueber die Einwirkung von Dinitrochlorbenzol auf Kaliumbenzoat und auf Acetamid," Berichte der Deutschen Hemischen Gesellschaft, 32, 3539-3540 (1899).

Pachter et al., "Methylation of Some Amides in Acetone," J. Am. Chem. Soc., 74, 1321-1322 (1952).

Rondestvedt Jr. "Aminations With Ammonia and Formamide. Synthesis of Terephtalamic Acid and of p-Nitroaniline," J. Org. Chem., 42(19), 3118-3123 (1977).

* cited by examiner

*Primary Examiner* — Rita J Desai
(74) *Attorney, Agent, or Firm* — Leydig, Voit & Mayer, Ltd.

(57) ABSTRACT

Provided is a process for producing highly pure 4-amino-1-isobutyl-1H-imidazo[4,5-c]quinoline (imiquimod), which includes reacting 4-chloro-1-isobutyl-1H-imidazo[4,5-c]quinoline with a non-gaseous amine precursor. Also provided are methods for isolating highly pure imiquimod. Further provided are intermediates useful in the production of imiquimod, methods for producing such intermediates, and methods for obtaining imiquimod from such intermediates.

20 Claims, No Drawings

IMIQUIMOD PRODUCTION PROCESS

BACKGROUND OF THE INVENTION 4-amino-1-isobutyl-1H-imidazo[4,5-c]quinoline, also known as imiquimod, is an immune response modifier, useful for treating genital warts. Imiquimod is also used for topical treatment of clinically typical nonhyperkeratotic, nonhypertrophic actinic keratoses on the face or scalp in immunocompetent adults and for the treatment of biopsy-confirmed, primary superficial basal cell carcinoma in immunocompetent adults, with a maximum tumor diameter of 2.0 cm, located on the trunk (excluding anogenital skin), neck, or extremities (excluding hands and feet). Imiquimod is marketed as a 5% cream under the trade name Aldara® and has the following structural formula (I):

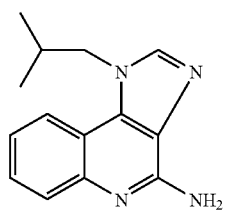

The synthesis of imiquimod is described in U.S. Pat. Nos. 4,689,338 and 4,929,624 (to Minnesota Mining and Manufacturing Co. Inc.). The processes described therein involve an ammonolysis reaction carried out by heating the compound 4-chloro-1-isobutyl-1-imidazo[4,5-c]quinoline of formula (II) in the presence of ammonium hydroxide or ammonia in methanol under high pressure (e.g. in a steel bomb) at 150° C. to afford imiquimod of formula (I), as depicted in Scheme 1.

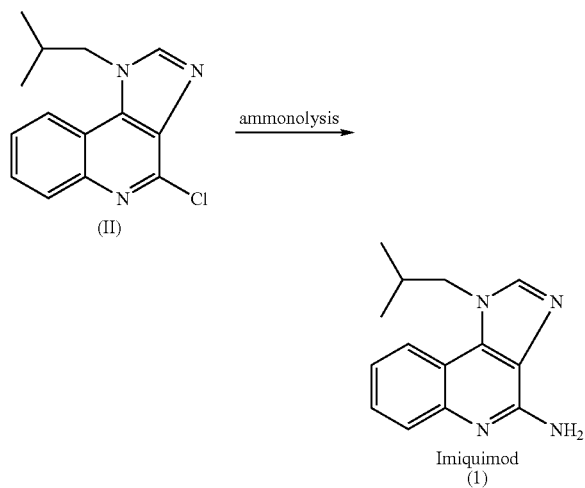

U.S. Pat. No. 4,988,815 describes a process for preparing imiquimod, which involves ammonolysis of the compound 4-chloro-1-isobutyl-1H-imidazo[4,5-c]quinoline.

Conventional processes using ammonolysis, e.g., as described in U.S. Pat. Nos. 4,689,338 and 4,929,624, are disadvantageous in that the reaction is conducted at high temperature and under pressure, which is undesirable with respect to industrial safety measures.

US Patent Application Publication No. 2005/0085500 discloses a process for preparing imiquimod in which 4-chloro-1-isobutyl-1H-imidazo[4,5-c]quinoline is converted to imiquimod in three steps. In the first step, 4-N-benzylamino)-1-isobutyl-1H-imidazo[4,5-c]quinoline is obtained by reacting 4-chloro-1-isobutyl-1H-imidazo[4,5-c]quinoline with large excess of benzylamine. In the second step, the acid addition salt of 4-(N-benzylamino)-1-isobutyl-1H-imidazo[4,5-c]quinoline is prepared, and in the third step imiquimod is obtained from the acid addition salt by reaction with NaOH. The above process is disadvantageous in that it is lengthy.

US Patent Application Publication No. 2006/0004202 discloses a process for preparing imiquimod in which 4-chloro-1-isobutyl-1H-imidazo[4,5-c]quinoline is converted to imiquimod by reaction with hydroxylamine in the presence of sodium acetate. However, imiquimod is obtained by this process in a relatively the low yield of 52%, which makes this process unattractive for industrial implementation.

International Patent Application Publication No. WO 2006/070379 discloses a process for preparing imiquimod in which 4-chloro-1-isobutyl-1H-imidazo-[4,5-c]quinoline is converted to 4-iodo-1-isobutyl-1H-imidazo[4,5-c]quinoline by reaction with sodium iodide in the acetone followed by converting the resulting 4-iodo-1-isobutyl-1H-imidazo[4,5-c]quinoline to imiquimod with methanolic ammonia at a temperature of 150-155° C. and high pressure. In this case, not only is the process lengthy (with the extra step of preparing the intermediate 4-iodo-1-isobutyl-1H-imidazo[4,5-c]quinoline) but also the reaction is conducted at high temperature and pressure.

Thus, there is a need for an improved process for preparing highly pure imiquimod starting from 4-chloro-1-isobutyl-1H-imidazo[4,5-c]quinoline, which is suitable for industrial use in comparison to conventional processes, and produces highly pure imiquimod in fewer steps and under more industrially viable conditions. The present invention provides such a process.

BRIEF SUMMARY OF THE INVENTION

The present invention provides a novel, simplified process for preparing 4-amino-1-isobutyl-1H-imidazo[4,5-c]quinoline (imiquimod) of formula (I), which avoids using gaseous ammonia. The process of the present invention preferably includes:

heating 4-chloro-1-isobutyl-1H-imidazo[4,5-c]-quinoline of formula (II) in an organic solvent and in the presence of a non-gaseous amine precursor, which preferably includes one or more amine precursors selected from guanidine and salts thereof (e.g., guanidine, guanidine carbonate, guanidine hydrochloride, and the like), urea, melamine, semicarbazide and salts thereof (e.g., semicarbazide hydrochloride and the like), carbamates (e.g., ethyl carbamate), 3-amino-1,2,4-triazine, 3-amino-1,2,4-triazole, and 4-amino-1,2,4-triazole, to produce a compound of formula (I);

isolating the compound of formula (I); and optionally purifying the obtained compound of formula (I).

Preferably, the reaction is carried out in an organic solvent in the presence of the non-gaseous amine precursor. Preferred non-gaseous amine precursors include guanidine (e.g., guanidine carbonate) and urea.

The present invention further provides a process for preparing the compound 1-isobutyl-1H-imidazo[4,5-c]quinolin-4-guanidine of formula (III)

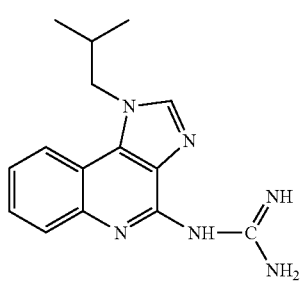

(III)

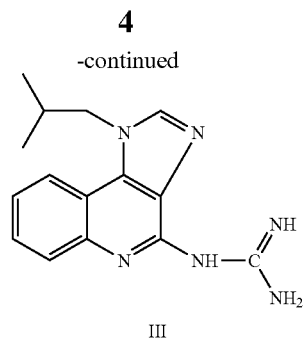

III which process preferably includes:
reacting a compound of formula (II) with guanidine carbonate in an organic solvent, preferably at a temperature of from about 130° C. to about 135° C.;
adding a base to the reaction mixture; and
isolating the product.

According to the present invention, the compound I-isobutyl-1H-imidazo[4,5-c]quinolin-4-guanidine (III) may be converted into imiquimod, e.g., by a process that includes:
hydrolyzing the compound of formula (III) at a temperature higher than 140° C.;
cooling the reaction mixture to ambient temperature and collecting crude imiquimod, e.g., by filtration; and
optionally purifying the crude imiquimod.

In accordance with the present invention, the crude compound of formula (I) can be optionally purified by a crystallization process that includes:
dissolving the imiquimod in an organic solvent, optionally at elevated temperature;
optionally adding a base to the solution;
optionally filtering the solution at elevated temperature;
cooling, e.g., to about 20° C., optionally with stirring, to produce imiquimod crystals;
collecting the crystals by filtration, and
washing the crystals, e.g., with at least one solvent and optionally drying the crystals.

DETAILED DESCRIPTION OF THE INVENTION

The present invention provides a novel, simplified process for preparing highly pure 4-amino-1-isobutyl-1H-imidazo[4,5-c]quinoline (imiquimod) of formula (I), which avoids using gaseous ammonia and working at elevated pressure. One embodiment of the process of the present invention is depicted in Scheme 2 below.

Scheme 2

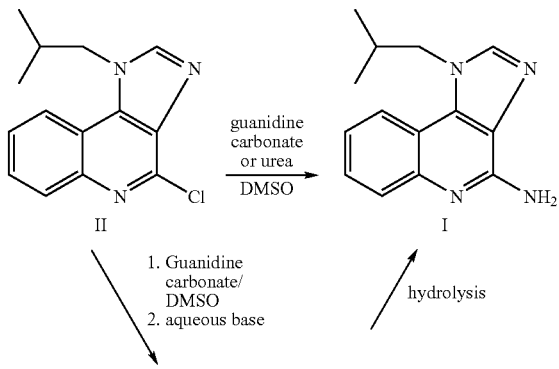

An exemplary process of the present invention includes:
heating 4-chloro-1-isobutyl-1H-imidazo[4,5-c]-quinoline of formula (II) in an organic solvent and in the presence of a non-gaseous amine precursor;
isolating the compound of formula (I); and
optionally purifying the obtained compound of formula (I).

The non-gaseous amine precursor is preferably selected from guanidine and salts thereof (e.g., guanidine, guanidine carbonate, guanidine hydrochloride, and the like), urea, melamine, semicarbazide and salts thereof (e.g., semicarbazide hydrochloride and the like), carbamates (e.g., ethyl carbamate), 3-amino-1,2,4-triazine, 3-amino-1,2,4-triazole, 4-amino-1,2,4-triazole, and the like, and combinations thereof. Preferred non-gaseous amine precursors include guanidine carbonate and urea.

Preferably, the reaction solvent for reacting the non-gaseous amine precursor with the compound of formula II includes dimethyl sulfoxide (DMSO), N-methyl-2-pyrrolidone (NMP), tetramethylene sulfone (sulfolane), diisoamyl ether, diglyme, triglyme, decahydronaphthalene, paraffins, and the like, or any mixture thereof. A particularly preferred solvent for reacting the non-gaseous amine precursor with the compound of formula IT is dimethyl sulfoxide (DMSO).

The progress of the reaction can be monitored using any suitable method, e.g., high performance liquid chromatography (HPLC) or thin layer chromatography (TLC), and the reaction may be stopped, e.g., after complete disappearance of the starting material as determined by the method used to monitor the reaction.

In one embodiment, the non-gaseous amine precursor is guanidine or a salt thereof. In accordance with the present invention, the reaction of guanidine or a salt thereof can be carried out in an organic solvent. In a preferred embodiment, about 2 equivalents of guanidine carbonate relative to one equivalent of the compound of formula (II) are used in the process, and the process is carried out at a temperature of from about 140° C. to about 150° C.

An exemplary guanidine salt, which can be used as the non-gaseous amine precursor, is guanidine carbonate [$H_2N$—$C(=NH)NH_2]_2.H_2CO_3$]. When guanidine carbonate is used as the non-gaseous amine precursor, the reaction with compound II is preferably carried out at elevated temperature. After completion of the reaction, the reaction mixture is preferably cooled, e.g., to ambient temperature, optionally with the addition of a base, to produce a solid, which can be collected by any suitable method, e.g., filtration. The resulting solid can be washed and dried, e.g., at elevated temperature and/or under reduced pressure, to yield crude imiquimod (I). Thus, the present invention provides a simple and straightforward method of preparing and isolating crude imiquimod simply by precipitating the compound from the reaction mixture. Preferably, the crude imiquimod is obtained by reaction of compound II with guanidine carbonate to produce imiquimod in high yield, which is preferably greater than 80%.

In another embodiment, the non-gaseous amine precursor is urea [$H_2N-CO-NH_2$]. When urea is used as the non-gaseous amine precursor, at least 5 equivalents of urea relative to one equivalent of the compound of formula (II) are preferably used in the reaction, and the reaction is preferably carried out at a temperature range of at least about 135° C., e.g., from about 135° C. to about 140° C. When urea is used as the non-gaseous amine precursor and the reaction is carried out at elevated temperature, the reaction mixture is preferably cooled after reaction completion, e.g., to a temperature of about 80° C., with the addition of water and a base (e.g., an aqueous NaOH solution) to produce a pH of 10-11, to precipitate imiquimod. The resulting mixture can be stirred at ambient temperature, e.g., for about 1 hour, and the crude imiquimod can be collected, e.g., by filtration.

Preferably, the reaction with urea in accordance with the process of the present invention produces crude imiquimod in high yield, which is preferably greater than 85%.

In yet another embodiment, the present invention provides a process for preparing the compound I-isobutyl-1H-imidazo[4,5-c]quinolin-4-guanidine of formula (III)

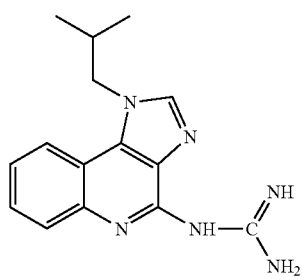

which preferably includes:

reacting a compound of formula (II) with guanidine carbonate in an organic solvent at a temperature of from about 130° C. to about 135° C.;

adding a base to the reaction mixture (e.g., with mixing) to produce the compound of formula (III); and isolating the compound of formula (III).

Preferably, the reaction with guanidine is carried out in the presence of about 2.5 equivalents of guanidine carbonate relative to one equivalent of the compound of formula (II), and is preferably carried out at a temperature range of from about 130° C. to about 135° C.

Preferred organic solvents used in the reaction with guanidine or a salt thereof include dimethyl sulfoxide (DMSO), N-methyl-2-pyrrolidone (NMP), tetramethylene sulfone (sulfolane), diisoamyl ether, diglyme, triglyme, decahydronaphthalene, paraffins, or any mixture thereof. A particularly preferred organic solvent for reacting guanidine or a salt thereof is dimethyl sulfoxide (DMSO).

Preferred bases include one or more bases selected from lithium hydroxide, sodium hydroxide, potassium hydroxide, cesium hydroxide, and the like, and combinations thereof. A particularly preferred base is sodium hydroxide.

In accordance with the present invention, the compound 1-isobutyl-1H-imidazo[4,5-c]quinolin-4-guanidine (III) may be further reacted to prepare imiquimod, e.g., by a process that includes:

hydrolyzing the compound of formula (III) at elevated temperature, e.g., at a temperature of at least about 140° C.;

cooling the reaction mixture, e.g., to ambient temperature, to precipitate crude imiquimod, optionally collecting the crude imiquimod, e.g., by filtration; and optionally purifying the crude imiquimod.

Preferably, the hydrolysis is carried out in a solvent mixture comprising an organic solvent, water and an acid. Preferred organic solvents for the hydrolysis reaction include one or more solvents selected from the N,N-dimethylacetamide (DMA), dimethyl sulfoxide (DMSO), N-methyl-2-pyrrolidone (NMP), and the like, and mixtures thereof. A particularly preferred solvent is dimethyl sulfoxide (DMSO). Preferred acids for the hydrolysis reaction include one or more acids selected from sulfuric acid, hydrochloric acid, hydrobromic acid, nitric acid, p-toluenesulfonic acid, and the like, and combinations thereof. A particularly preferred acid for the hydrolysis reaction is sulfuric acid.

Thus, preparing and optionally isolating the compound of formula (III) in accordance with the present invention allows imiquimod to be produced at relatively lower temperatures.

In accordance with the present invention, purifying the crude compound of formula (I) can be carried out by any suitable method, which can include, without limitation; precipitation, crystallization, slurrying, washing in a suitable solvent, filtration (e.g., through a packed-bed column), dissolution in an appropriate solvent (e.g., dimethyl sulfoxide (DMSO)) and re-precipitation by addition of at least one additional solvent (e.g., a second solvent) in which the compound is insoluble, and any combination of such methods. Preferably, the crude imiquimod produced in accordance with the present invention is purified by crystallizing imiquimod from a solvent, e.g., by a method that preferably includes:

dissolving the imiquimod in a solvent, optionally at elevated temperature;

optionally adding a base and mixing;

optionally filtering the solution at elevated temperature;

cooling, e.g., to ambient temperature, optionally with stirring, to produce imiquimod crystals;

collecting the crystals, e.g., by filtration, optionally washing the crystals, e.g., with at least one solvent, and optionally drying the crystals.

Preferred crystallization solvents include one or more solvents selected from water, N,N-dimethylformamide (DMF), N,N-dimethylacetamide (DMA), dimethyl sulfoxide (DMSO), N-methyl-2-pyrrolidone AMP), and the like, and mixtures thereof. A particularly preferred crystallization solvent is dimethyl sulfoxide (DMSO).

Preferred bases, which can be used in the crystallization process, include one or more bases selected from lithium hydroxide, sodium hydroxide, potassium hydroxide, cesium hydroxide, and the like, and combinations thereof: A particularly preferred base, which can be used in the crystallization process, includes sodium hydroxide.

Preferred solvents, which can be used for washing the imiquimod crystals, include one or more solvents selected from water, methanol, ethanol, 1-propanol, 2-propanol, and the like, and mixtures thereof. Particularly preferred solvents for washing the crystals include water, methanol, and mixtures thereof:

Crystallizing imiquimod in accordance with the present invention provides a highly pure product having a purity of at least about 98.5%, and preferably having a purity of at least about 99.5%, and more preferably having a purity of at least about 99.8%.

The following examples further illustrate the invention but, of course, should not be construed as in any way limiting its scope.

EXAMPLE 1

This example illustrates an exemplary process for preparing imiquimod by reaction of compound II with 10 equivalents of urea in DMSO at 135-140° C.

A mixture of 4-chloro-1-isobutyl-1H-imidazo[4,5-c]quinoline (II) (3 g, 0.0116 mol), urea (6.9 g, 0.116 mol, 10 equiv.) and DMSO (20 ml) was heated under stirring at 140° C. for 35 hours. Then, the reaction mixture was cooled to 80° C. and water (30 ml) and 46% aqueous NaOH solution were added to produce a pH of 10-11. The mixture was stirred at ambient temperature for 1 hour and a precipitate was collected by filtration. The wet compound was treated with water (20 ml) at 70-80° C. under stirring for 1 hour. A solid was collected by filtration from the hot mixture, washed with water (3×20 ml) and methanol (20 ml) and dried at 80° C. under reduced pressure overnight to yield 2.4 g of crude Imiquimod in 87.6% yield, having 99.0% purity (by HPLC, containing 1.0% of compound II).

A mixture of the crude product (2.4 g) and DMSO (45 ml) was heated under stirring at 140° C. to obtain a solution. 46% aqueous NaOH solution was added drop-wise to the solution to produce a pH of 10-11. The mixture was stirred at 140° C. for 1 hour. A sample was withdrawn and injected to an HPLC system. According to the HPLC chromatogram the product contained 0.07% of compound II. The hot solution was filtered and the filtrate was cooled to ambient temperature and kept at 20-25° C. for 8 hours. A precipitate was collected by filtration, washed with water (3×20 ml) and methanol (2×10 ml) and dried at 80° C. overnight to obtain 2.1 g of imiquimod in 87.8% yield; total yield: 77.0%, having a purity of 99.94% (by HPLC).

EXAMPLE 2

This example illustrates an exemplary process for preparing imiquimod by reaction of compound II with 20 equivalents of urea in DMSO at 155-160° C.

A mixture of 4-chloro-1-isobutyl-1H-imidazo[4,5-c]quinoline (II) (3 g, 0.0116 mol), urea (13.8 g, 0.232 mol, 20 equiv.) and DMSO (25 ml) was heated under stirring at 155-160° C. for 12 hours. Then, the reaction mixture was cooled to 80° C. and water (30 ml) and 46% aqueous NaOH solution were added to produce a pH of 10-11. The mixture was stirred at ambient temperature for 1 hour and a precipitate was collected by filtration. The wet compound was treated with water (20 ml) at 70-80° C. under stirring for 1 hour. A solid was collected by filtration from the hot mixture, washed with water (3×20 ml) and methanol (20 ml) and dried at 80° C. under reduced pressure overnight to yield 2.45 g of crude imiquimod in 88.5% yield, having a purity of 99.0% (by HPLC, containing 1.0% of the compound II). The crude imiquimod was purified by the method presented in Example 1 to obtain 2.15 g of imiquimod in 87.8% yield; total yield: 77.7%; having a purity of 99-93% (by HPLC).

EXAMPLE 3

This example illustrates an exemplary process for preparing imiquimod by reaction of compound II with 20 equivalents of urea in DMSO at 145-150° C.

A mixture of 4-chloro-1-isobutyl-1H-imidazo[4,5-c]quinoline (II) (4 g, 0.0154 mol), urea (18.5 g, 0.308 mol, 20 equiv.) and DMSO (26 ml) was heated under stirring at 145-150+C for 24 hours. Then, the reaction mixture was cooled to 80° C. and water (52 ml) and 46% aqueous NaOH solution were added to produce a pH of 10-11. The mixture was stirred at ambient temperature for 1 hour and a precipitate was collected by filtration. The wet compound was treated with water (25 ml) at 70-80° C. under stirring for 1 hour. A solid was collected by filtration from the hot mixture, washed with water (3×20 ml) and methanol (20 ml) and dried at 80° C. under reduced pressure overnight to yield 3.13 g of crude imiquimod in 84.8% yield, having a purity of 99.4% by HPLC, (containing 0.6% of the compound II). The crude imiquimod was purified by the method presented in Example 1 to obtain 2.75 g of imiquimod in 87.8% yield; total yield: 74.4%; having a purity of 99.93% (by HPLC).

EXAMPLE 4

This example illustrates an exemplary process for preparing 1-isobutyl-1H-imidazo[4,5-c]quinolin-4-guanidine (III).

A mixture of 4-chloro-1-isobutyl-1H-imidazo[4,5-c]quinoline (II) (9.0 g, 0.0346 mol), guanidine carbonate (15.6 g, 0.0866 mol, 2.5 molar equiv.) and DMSO (50 ml) was heated under stirring at 130-135+C for 5.5 hours. Then, the reaction mixture was cooled to 60° C. and water (90 ml) and 46% aqueous NaOH solution were added to produce a pH of 10-11. The mixture was stirred at ambient temperature for 2 hours and a precipitate was collected by filtration, washed with water (3×40 ml) and methanol (35 ml) and dried at 80° C. under reduced pressure overnight to yield 7.1 g of crude compound III, having a purity of 93.5% (by HPLC). The crude compound III was purified via its hydrochloride salt to yield 1-isobutyl-1H-imidazo[4,5-c]quinolin-4-guanidine (III), having a purity of 99.7% by HPLC); mp 226-228° C.

NMR $^{13}$C (DMSO-d$_6$). δ=19.27 2CH$_3$, 28.36 [CH(CH$_3$)$_2$], 53.41 (CH$_2$), 115.25, 120.27, $\overline{122.60}$, 126.$\overline{65}$, 126.94, 132.16, $\overline{133.06}$, and 143.11 (C$_{arom.}$), 143.52 (N—CH=N), 155.19 [N=C(NH—)C], and 159.12 [H$_2$N—$\underline{C}$(=NH)NH—]. ESI $\overline{MS}$ (m/z): 283.3 [MH$^+$].

EXAMPLE 5

This example illustrates an exemplary process for preparing imiquimod by reaction of compound II with 2 molar equivalents of guanidine carbonate in DMSO at 140-150° C.

A mixture of 4-chloro-1-isobutyl-1H-imidazo[4,5-c]quinoline (II) (6.0 g, 0.0232 mol), guanidine carbonate (8.4 g, 0.0466 mol, 2.0 molar equiv.) and DMSO (50 ml) was heated under stirring at 140-150° C. for 1 hour. A sample was withdrawal and injected to an HPLC system. According to the HPLC chromatogram the product contained 5.76% of imiquimod, 93.58% of the compound III and 0.66% of the compound II in the reaction mixture. Stirring was continued at 140-150° C. for Her 9 hours, after which time a sample was withdrawn and injected to an HPLC system. According to the HPLC chromatogram the product contained 99.4% of imiquimod and 0.6% of compound III. Then, the reaction mixture was cooled to ambient temperature and a precipitate was collected by filtration, washed with water (3×40 ml) and methanol (35 ml) and dried at 80° C. under reduced pressure overnight to yield 4.5 g of crude Imiquimod in 81.2% yield, having a purity of 99.85% (by HPLC).

The crude imiquimod (4.5 g) was dissolved in DMSO (80 ml) at 140° C. The hot solution was filtered off and the filtrate was kept at 20° C. overnight. A precipitate was collected by filtration, washed with water (3×20 ml) and methanol (3×10 ml) and dried at 80° C. under reduced pressure overnight to obtain 4.0 g of pure imiquimod in 87.8% yield, overall yield: 71.3%; having a purity of 99.93% (by HPLC).

EXAMPLE 6

This example illustrates an exemplary process for producing imiquimod by reaction of a compound III with sulfuric acid in DMSO at 140° C.

A mixture of 1-isobutyl-1H-imidazo[4,5-c]quinolin-4-guanidine (III) (10.0 g, 0.0357 mol), 95-98% sulfuric acid (0.5 ml), water (2 ml) and DMSO (50 ml) was heated under stirring at 140° C. for 20 hours. Then, the reaction mixture was cooled to 60° C. and water (100 ml) was added followed by addition of 46% aqueous NaOH solution drop-wise to produce a pH of 10-11. The mixture was stirred at ambient temperature for 2 hours and a precipitate was collected by filtration, washed with water (3×40 ml) and methanol (35 ml) and dried at 80° C. under reduced pressure overnight to yield 6 g, of crude compound I, in 70% yield.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A process for preparing 4-amino-1-isobutyl-1H-imidazo[4,5-c]quinoline (imiquimod) of formula (I), the process comprising:
   reacting 4-chloro-1-isobutyl-1H-imidazo[4,5-c]-quinoline of formula (II) in an organic solvent with a non-gaseous amine precursor, which is guanidine or a salt thereof, or urea, to produce the compound of formula (I);
   isolating the compound of formula (I); and
   optionally purifying the compound of formula (I).

2. The process of claim 1, wherein the organic solvent comprises dimethyl sulfoxide (DMSO), N-methyl-2-pyrrolidone (NMP), tetramethylene sulfone (sulfolane), diisoamyl ether, diglyme, triglyme, decahydronaphthalene, paraffins, or a mixture thereof.

3. The process of claim 2, wherein the organic solvent is dimethyl sulfoxide (DMSO).

4. The process of claim 1, wherein the non-gaseous amine precursor is guanidine carbonate.

5. The process of claim 1, wherein said reacting comprises heating the compound of formula (II) and guanidine carbonate in the organic solvent at a temperature of from about 140° C. to about 150° C. optionally without application of pressure.

6. The process of claim 5, wherein about 2 equivalents of guanidine carbonate are used per 1 equivalent of the compound of formula (II).

7. The process of claim 1, wherein the non-gaseous amine precursor is urea.

8. The process of claim 7, wherein the urea and the compound of formula (II) are heated at a temperature of from about 135° C. to about 140° C., optionally without application of pressure.

9. The process of claim 8, wherein at least about 5 equivalents of urea are used per 1 equivalent of the compound of formula (II).

10. The process of claim 1, comprising isolating the imiquimod from the reaction mixture and purifying the imiquimod by one or more methods selected from precipitation, crystallization, slurrying, washing with a suitable solvent, filtration, re-precipitation from a solvent system comprising at least one solvent and at least one additional solvent in which the imiquimod is insoluble, and combinations thereof.

11. The process of claim 10, wherein the imiquimod is purified by a crystallization method comprising:
   dissolving the imiquimod in a solvent, optionally at elevated temperature;
   optionally adding a base and mixing;
   optionally filtering the solution at elevated temperature;
   optionally cooling to about 20° C. to produce imiquimod crystals; and
   collecting imiquimod crystals, optionally washing the crystals with at least one solvent, and optionally drying the crystals.

12. The process of claim 11, wherein the crystallization solvent is water, dimethyl sulfoxide (DMSO), N,N-dimethylformamide (DMF), N,N-dimethylacetamide (DMA), N-methyl-2-pyrrolidone (NMP), or a mixture thereof.

13. The process of claim 12, wherein the crystallization solvent is dimethyl sulfoxide (DMSO).

14. The process of claim 11, wherein the base is lithium hydroxide, sodium hydroxide, potassium hydroxide, cesium hydroxide, or a combination thereof.

15. The process of claim 14, wherein the base is sodium hydroxide.

16. The process of claim 11, wherein the solvent used for washing the crystals is water, methanol, ethanol, 1-propanol, 2-propanol, or a mixture thereof.

17. The process of claim 16, wherein the solvent is water, methanol or a mixture thereof.

18. The process of claim 11, wherein 4-amino-1-isobutyl-1H-imidazo[4,5-c]quinoline (imiquimod) (I) is obtained in a purity of at least about 98.5%.

19. The process of claim 18, wherein 4-amino-1-isobutyl-1H-imidazo[4,5-c]quinoline (imiquimod) (I) is obtained in a purity of at least about 99.5%.

20. The process of claim 19, wherein 4-amino-1-isobutyl-1H-imidazo[4,5-c]quinoline (imiquimod) (I) is obtained in a purity equal to or greater than about 99.8%.

* * * * *